(12) United States Patent
Igarashi et al.

(10) Patent No.: US 9,811,907 B2
(45) Date of Patent: Nov. 7, 2017

(54) MEDICAL IMAGE PROCESSING APPARATUS AND MEDICAL IMAGE PROCESSING METHOD

(71) Applicant: Toshiba Medical Systems Corporation, Otawara-shi (JP)

(72) Inventors: Takuma Igarashi, Nasushiobara (JP); Satoshi Wakai, Nasushiobara (JP); Kazumasa Arakita, Nasushiobara (JP); Hideaki Ishii, Nasushiobara (JP); Yasuko Fujisawa, Nasushiobara (JP); Shigeo Kaminaga, Otawara (JP); Kenji Hirohata, Tokyo (JP); Junichiro Ooga, Tokyo (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/726,158

(22) Filed: May 29, 2015

(65) Prior Publication Data
US 2015/0262357 A1    Sep. 17, 2015

Related U.S. Application Data

(63) Continuation of application No. PCT/JP2013/082278, filed on Nov. 29, 2013.

(30) Foreign Application Priority Data

Nov. 30, 2012  (JP) .................................. 2012-263565
Nov. 30, 2012  (JP) .................................. 2012-263566
Nov. 29, 2013  (JP) .................................. 2013-248490

(51) Int. Cl.
*G06T 7/00*     (2017.01)
*A61B 6/03*     (2006.01)
(Continued)

(52) U.S. Cl.
CPC ............ *G06T 7/0014* (2013.01); *A61B 6/032* (2013.01); *A61B 6/463* (2013.01); *A61B 6/504* (2013.01);
(Continued)

(58) Field of Classification Search
None
See application file for complete search history.

(56) References Cited

U.S. PATENT DOCUMENTS 8,010,175 B2 *  8/2011  O'Donnell ............. G06T 7/149
                                                   600/407
9,196,037 B2 * 11/2015  Jung ..................... G06T 7/0012
(Continued)

FOREIGN PATENT DOCUMENTS

JP   2007-151881 A    6/2007
JP   2009-028515 A    2/2009
(Continued)

OTHER PUBLICATIONS

Zijlstra F, Van Ommeren J, Reiber JH, Serruys PW. Does the quantitative assessment of coronary artery dimensions predict the physiologic significance of a coronary stenosis?. Circulation. Jun. 1, 1987;75(6):1154-61.*

(Continued)

*Primary Examiner* — Michelle Hausmann
(74) *Attorney, Agent, or Firm* — Oblon, McClelland, Maier & Neustadt, L.L.P.

(57) ABSTRACT

There is provided a medical image processing apparatus which includes a first extraction unit configured to extract coronary arteries depicted in images of a plurality of time phases relating to the heart, and to extract at least one stenosed part depicted in each coronary artery; a calculation unit configured to calculate a pressure gradient of each of the extracted coronary arteries, based on tissue blood flow (Continued)

volumes of the coronary arteries; a second extraction unit configured to extract an ischemic region depicted in the images; and a specifying unit configured to specify a responsible blood vessel of the ischemic region by referring to a dominance map, in which each of the extracted coronary arteries and a dominance territory are associated, for the extracted ischemic region, and to specify a responsible stenosis, based on the pressure gradient corresponding to a stenosed part in the specified responsible blood vessel.

10 Claims, 18 Drawing Sheets

(51) Int. Cl.
*A61B 6/00* (2006.01)
*G06T 11/00* (2006.01)

(52) U.S. Cl.
CPC .......... *A61B 6/5211* (2013.01); *A61B 6/5217* (2013.01); *G06T 7/0016* (2013.01); *G06T 11/003* (2013.01); *A61B 6/503* (2013.01); *A61B 6/507* (2013.01); *G06T 2200/04* (2013.01); *G06T 2207/10016* (2013.01); *G06T 2207/10076* (2013.01); *G06T 2207/10081* (2013.01); *G06T 2207/30048* (2013.01); *G06T 2207/30104* (2013.01)

(56) References Cited

U.S. PATENT DOCUMENTS

| | | | |
|---|---|---|---|
| 2008/0133000 A1* | 6/2008 | Molony | A61F 2/88 623/1.35 |
| 2009/0010519 A1 | 1/2009 | Wakai et al. | |
| 2009/0143654 A1* | 6/2009 | Funane | A61B 5/14553 600/309 |
| 2011/0060234 A1* | 3/2011 | Zhou | A61B 5/04011 600/509 |
| 2012/0041739 A1 | 2/2012 | Taylor | |
| 2012/0063663 A1* | 3/2012 | Kawasaki | G06T 7/0014 382/133 |
| 2012/0207371 A1 | 8/2012 | Wakai et al. | |
| 2015/0262357 A1* | 9/2015 | Igarashi | G06T 7/0016 382/131 |

FOREIGN PATENT DOCUMENTS

| | | |
|---|---|---|
| JP | 2009-273815 A | 11/2009 |
| JP | 2010-104710 A | 5/2010 |
| JP | 2012-081254 A | 4/2012 |
| WO | WO 2010/098444 A1 | 9/2010 |
| WO | WO 2012/021307 A2 | 2/2012 |

OTHER PUBLICATIONS

Xu, Wenlong, Ling Xia, and Weixue Lu. "Studies of coronary artery stenosis with heart-torso model." Engineering in Medicine and Biology Society, 1998. Proceedings of the 20th Annual International Conference of the IEEE. IEEE.*

L'abbate, G. A., et al. "Integration of multimodal data of cardiac diseases in a dynamic three-dimensional heart model." Computers in Cardiology, 1999. IEEE, 1999.*

Park, Ye-Seul, Meeyeon Lee, and Jung-Won Lee. "Template-Driven Medical Imaging Information Providing Process Using Semantic Relations Targeting Acute Myocardial Infarction." Innovative Mobile and Internet Services in Ubiquitous Computing (IMIS), 2016 10th International Conference on. IEEE, 2016.*

Beliveau, Pascale, et al. "Computation of coronary perfusion territories from CT angiography." Computers in Cardiology, 2007. IEEE, 2007.*

International Search Report mailed Mar. 4, 2014 for PCT/JP2013/082278 filed Nov. 29, 2013 with English Translation.

International Written Opinion mailed Mar. 4, 2014 for PCT/JP2013/082278 filed Nov. 29, 2013.

James K. Min, et al., "Rationale and design of the DeFACTO(Determination of Fractional Flow Reserve by Anatomic Computed Tomographic AngiOgraphy) study", Journal of Cardiovascular Computed Tomography, 2011, vol. 5, pp. 301-309.

* cited by examiner

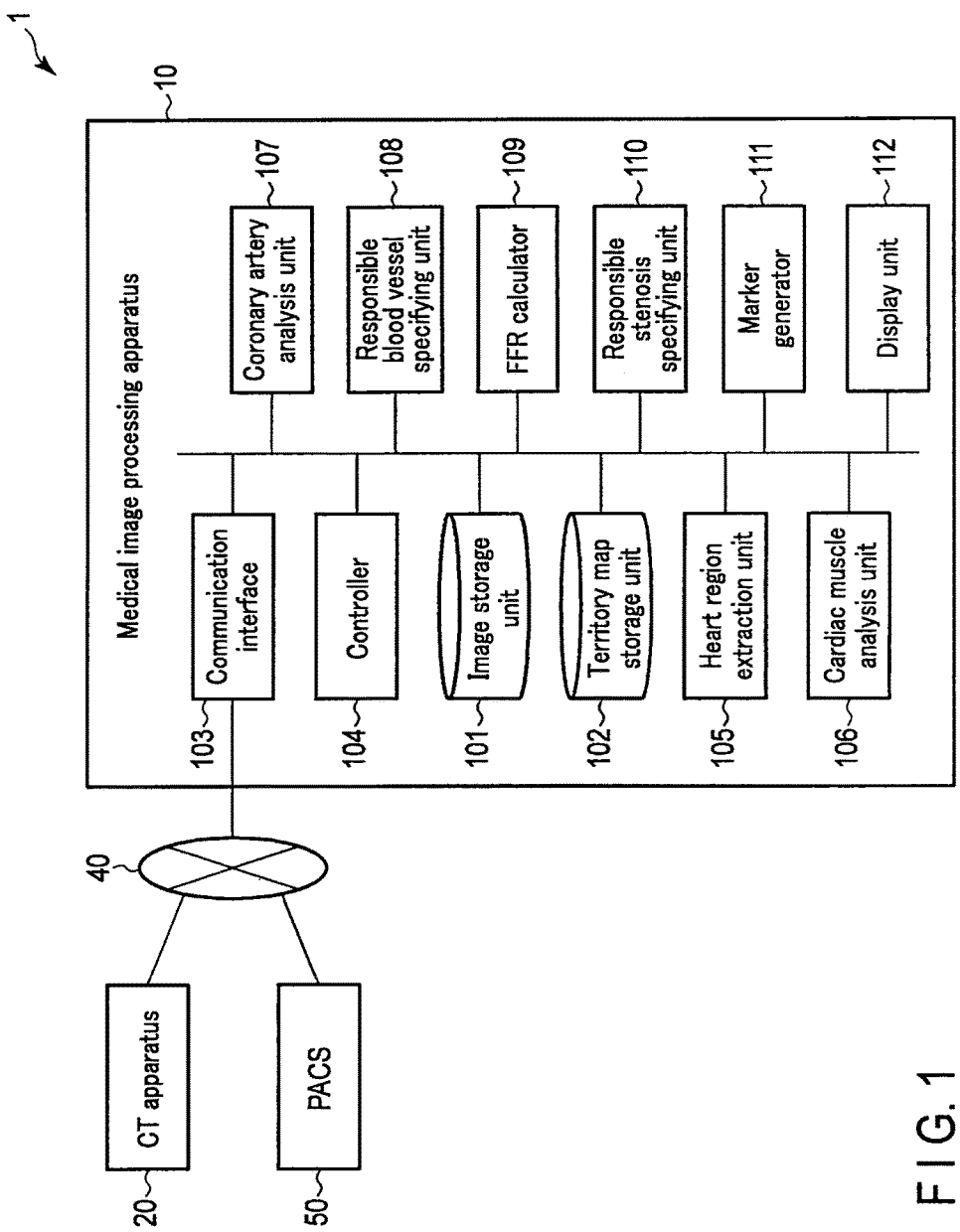
F I G. 1

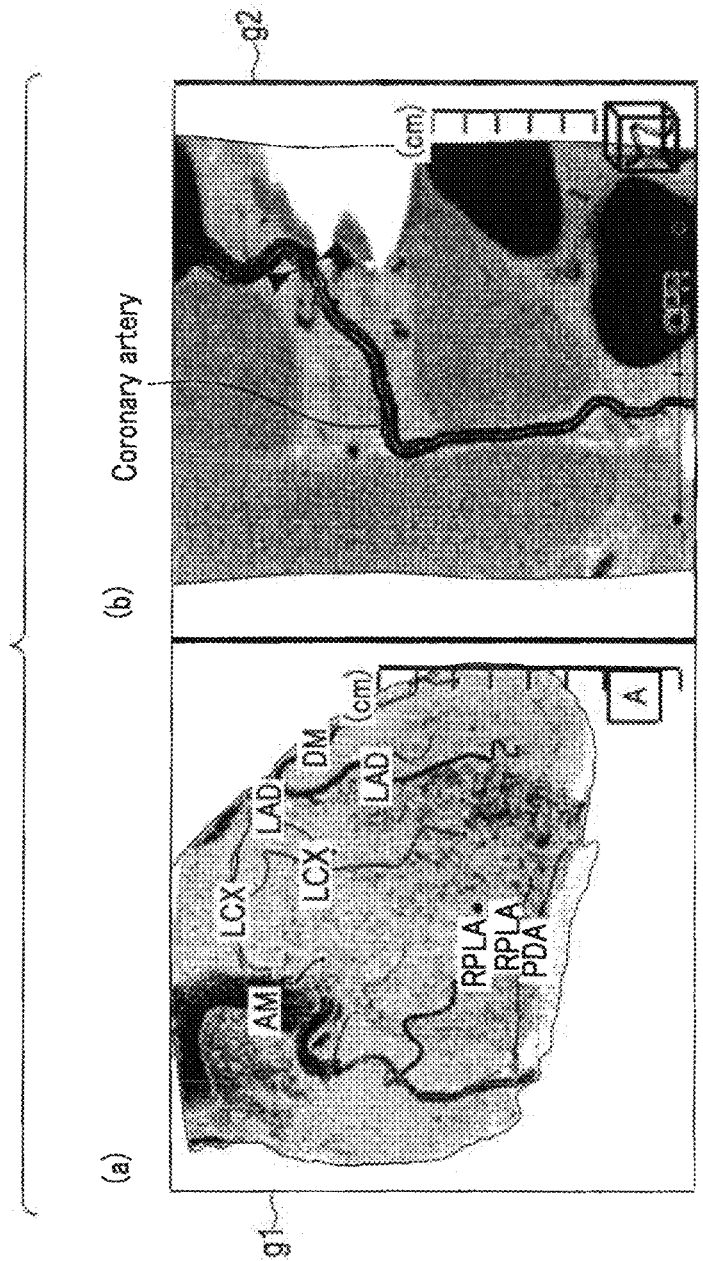
F I G. 4

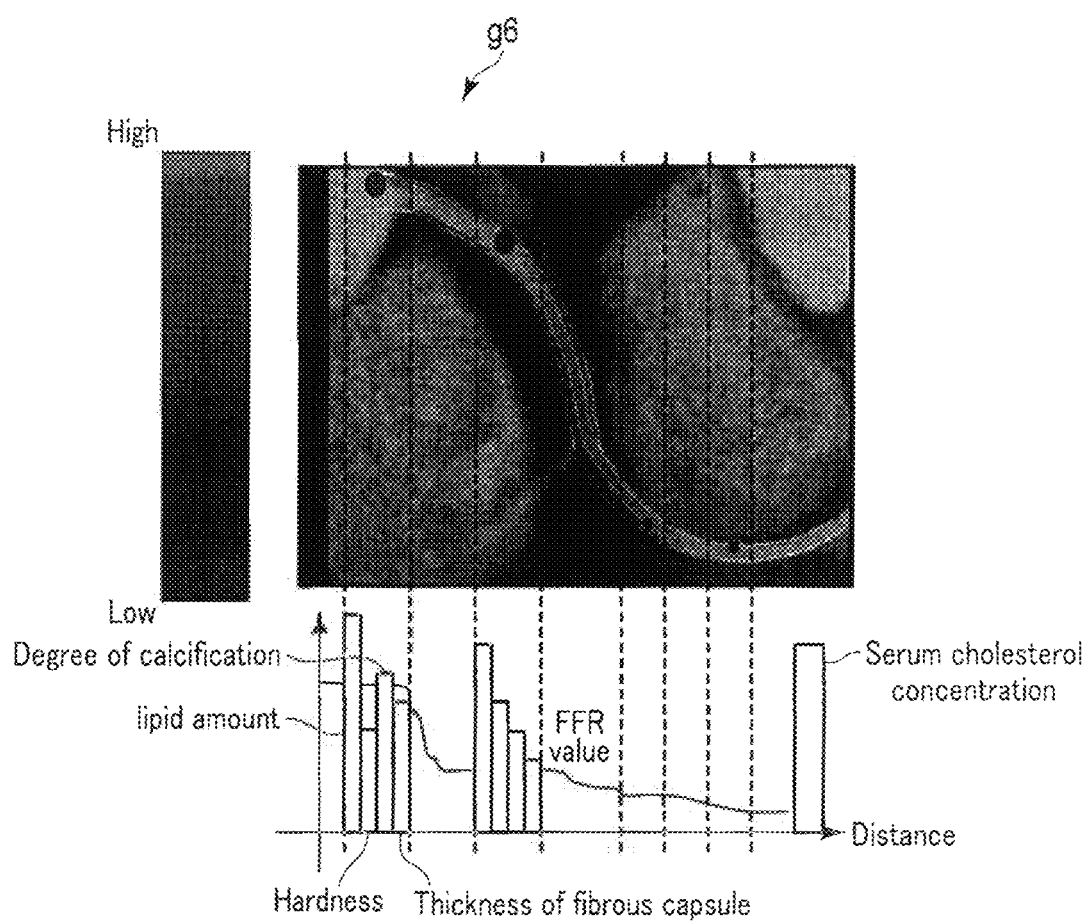
F I G. 8A

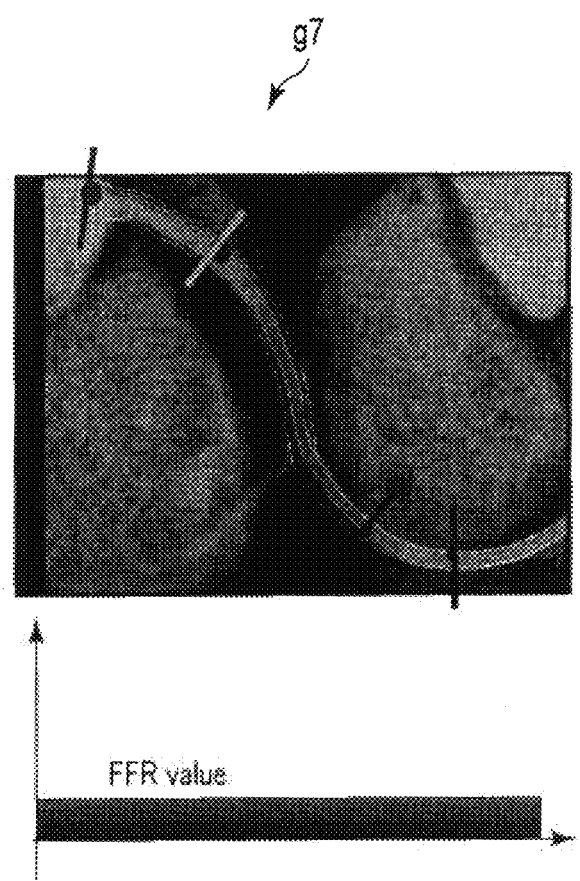
F I G. 8B

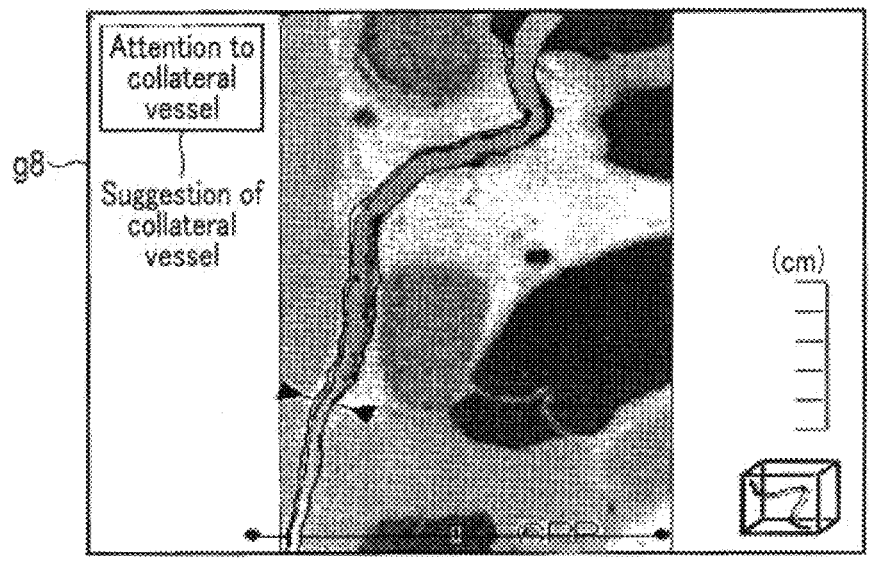
F I G. 9
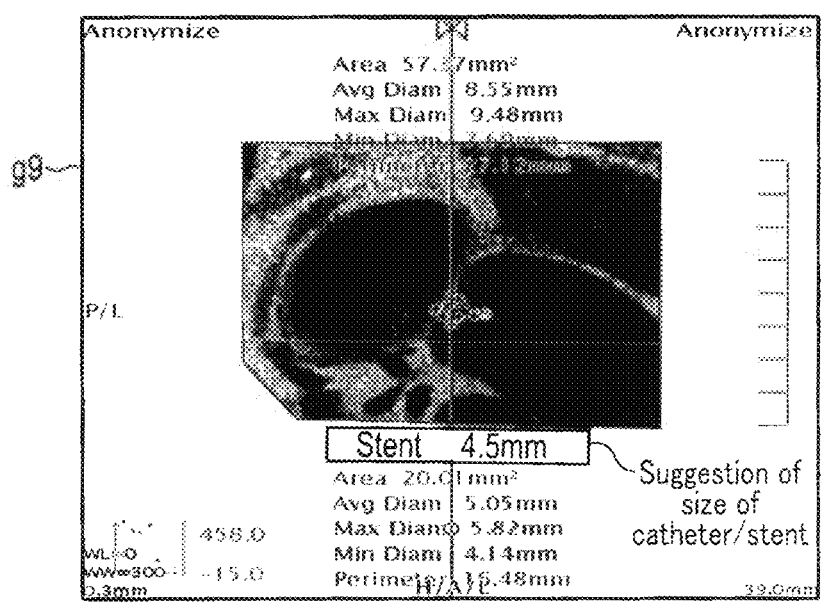
F I G. 10

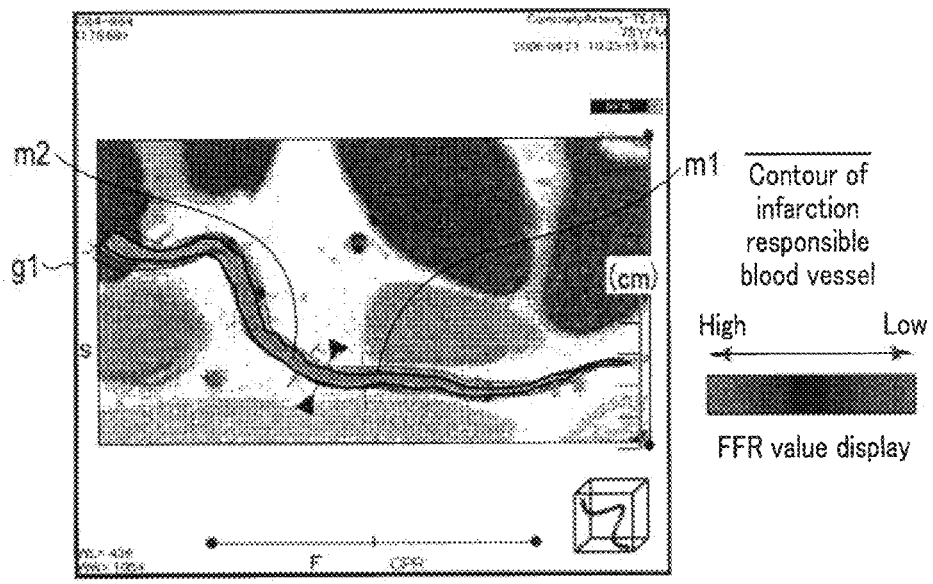
F I G. 15
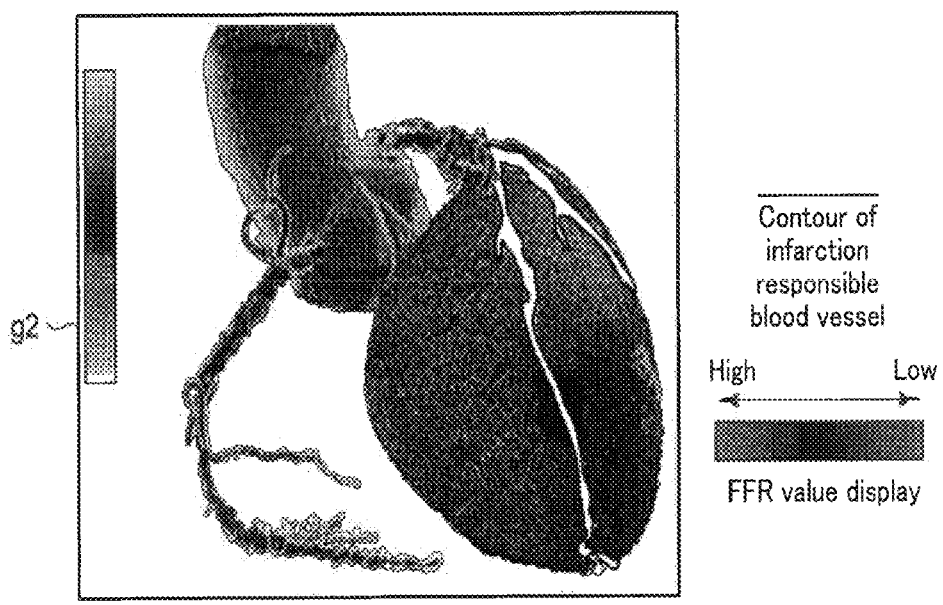
F I G. 16

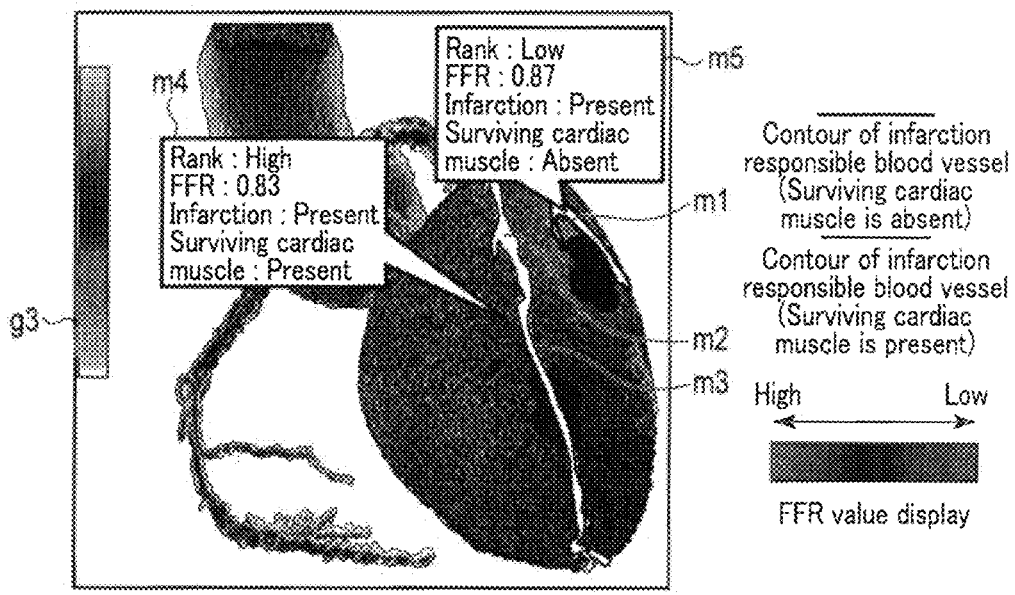
F I G. 19

MEDICAL IMAGE PROCESSING APPARATUS AND MEDICAL IMAGE PROCESSING METHOD

CROSS-REFERENCE TO RELATED APPLICATIONS

This application is a Continuation Application of PCT Application No. PCT/JP2013/082278, filed Nov. 29, 2013 and based upon and claiming the benefits of priority from Japanese Patent Applications No. 2013-248490, filed Nov. 29, 2013, No. 2012-263565, filed Nov. 30, 2012, and No. 2012-263566, filed Nov. 30, 2012, the entire contents of all of which are incorporated herein by reference.

FIELD

Embodiments of the present invention relate to a medical image processing apparatus or a medical image processing method.

BACKGROUND

In general, in ischemic heart diseases, a blood flow to the cardiac muscle is hindered due to occlusion, stenosis, etc. of a coronary artery, and the supply of blood becomes deficient or stops, leading to a failure of the heart. A symptom is a sensation of pain or compression mainly in the precordia or, in some cases, in the left arm or in the back. Therapeutic methods for patients with ischemic heart diseases are generally classified into bypass surgery, PCI (catheter surgery), and pharmacotherapy.

The bypass surgery is a therapeutic method in which, as illustrated in FIG. 20, some other blood vessel is connected to a blood vessel which is stenosed or occluded, thereby causing more blood to flow through this connected blood vessel to a region in which ischemia occurs.

PCI is a therapeutic method in which, as illustrated in FIG. 21 and FIG. 22, a therapeutic instrument with a thin tubular structure is directly inserted in a blood vessel in which occlusion or stenosis occurs, thereby forcibly expanding the blood vessel.

The pharmacotherapy is a therapeutic method for improving ischemia of the heart, or preventing formation of a thrombus.

There is known FFR (Fractional Flow Reserve) as an index which a doctor refers to when selecting any one of these three therapeutic methods.

In general, assessment of the degree of progress of stenosis is carried out by directly inserting a pressure wire into a blood vessel. The pressure wire is inserted, as illustrated in FIG. 23, and pressures $P_{in}$ and $P_{out}$ at regions in front of and behind a stenosed part are measured.

Here, the FFR is defined by $P_{out}/P_{in}$. If this value is lower than 0.8, the doctor selects the PCI as the therapeutic method. If this value is higher than 0.8, the doctor selects pharmacotherapy as the therapeutic method. However, since the measurement of the pressures $P_{in}$ and $P_{out}$ with use of the pressure wire is invasive, there is a demand for a non-invasive measuring method and FFR estimation method.

This being the case, in recent years, a simulation-based FFR estimation method using fluid analysis has been devised. An existing simulation is a simulation using 3D images. In the basic concept of such a simulation-based FFR estimation method, the shape of a blood vessel, which is obtained from modality, and physical parameters, such as a viscosity value, etc. of blood, etc., are used as inputs, and FFR is estimated (calculated) by using a Navier-Stokes equation which is used in, e.g. CFD (Computational Fluid Dynamics).

A problem with such 3D simulation is that a great deal of calculation time is required. Thus, such a problem arises that time is also needed until selecting a therapeutical method by using the FFR, and the 3D simulation is not suitable when there is no time to lose. As a measure for an improvement, there is a method in which the time needed for simulation is greatly reduced by executing 2D approximation of the simulation that uses 3D images.

Thereby, it becomes possible to quickly calculate FFR on the basis of simulation, and the doctor can use FFR as an effective index.

At present, however, it is not possible to assess the causal relationship between an ischemic cardiac muscle and a stenosed part to be treated, or to make risk assessment. Specifically, the FFR fails to be properly reflected on the assessment of the causal relationship between an ischemic cardiac muscle and a stenosed part to be treated, and on the risk assessment. Judgment as to, for example, which stenosed part is to be treated with top priority depends greatly on the empirical rule of doctors. Thus, such a problem arises that there is a concern of occurrence of a human error, such as unnecessary treatment or an oversight.

In addition, for example, in a coronary artery which contributes to myocardial infarction, since the blood flow volume and pressure decrease, the FFR apparently increases. Thus, despite such a serious symptom as myocardial infarction having been caused, the FFR is apparently high. In this case, too, such a problem arises that there is a concern of occurrence of a human error, such as an oversight of a symptom, or erroneous selection of a therapeutic method.

The object is to provide a medical image processing apparatus which can reduce the possibility of a human error.

BRIEF DESCRIPTION OF THE DRAWINGS

FIG. 1 is a schematic view illustrating a configuration example of a medical image processing system including a medical image processing apparatus according to a first embodiment.

FIG. 4 is a schematic view illustrating an example of an analysis result by a coronary artery analysis unit according to the first embodiment.

FIG. 8A is a schematic view illustrating an example of a two-dimensional image of a responsible blood vessel which is displayed by the display unit according the first embodiment, the two-dimensional image suggesting the degree of priority of treatment.

FIG. 8B is a schematic view illustrating an example of a two-dimensional image of a responsible blood vessel which is displayed by the display unit according the first embodiment, the two-dimensional image suggesting the degree of priority of treatment.

FIG. 9 is a schematic view illustrating an example of a two-dimensional image of a responsible blood vessel which is displayed by the display unit according the first embodiment, the two-dimensional image suggesting the presence of a collateral vessel.

FIG. 10 is a schematic view illustrating an example of a two-dimensional image of a responsible blood vessel which is displayed by the display unit according the first embodiment, the two-dimensional image suggesting the size of a catheter/stent.

FIG. 15 is a schematic view illustrating an example of a two-dimensional image of an infarction responsible blood vessel which is displayed by a display unit according the second embodiment.

FIG. 16 is a schematic view illustrating an example of a three-dimensional image of an infarction responsible blood vessel which is displayed by the display unit according the second embodiment.

FIG. 19 is a schematic view illustrating an example of a three-dimensional image of an infarction responsible blood vessel which is displayed by a display unit according the third embodiment.

DETAILED DESCRIPTION

First Embodiment

A medical image processing apparatus disclosed by this embodiment comprises a first extraction unit, a calculation unit, a second extraction unit, a specifying unit and a display. The first extraction unit is implemented by processing circuitry and configured to extract a plurality of coronary arteries depicted in data of images of a plurality of time phases relating to the heart, and to extract at least one stenosed part depicted in each of the extracted coronary arteries. The calculation unit is implemented by processing circuitry and configured to calculate a pressure gradient of each of the extracted coronary arteries, based on tissue blood flow volumes of the plurality of extracted coronary arteries. The second extraction unit is implemented by processing circuitry and configured to extract an ischemic region depicted in the images. The specifying unit is implemented by processing circuitry and configured to specify a responsible blood vessel of the ischemic region by referring to a dominance map, in which each of the extracted coronary arteries and a dominance territory are associated, for the extracted ischemic region, and to specify a responsible stenosis, based on the pressure gradient corresponding to a stenosed part in the specified responsible blood vessel. The display is configured to display an image in which the specified responsible stenosis is depicted, together with information indicative of the responsible stenosis.

Figure 2:
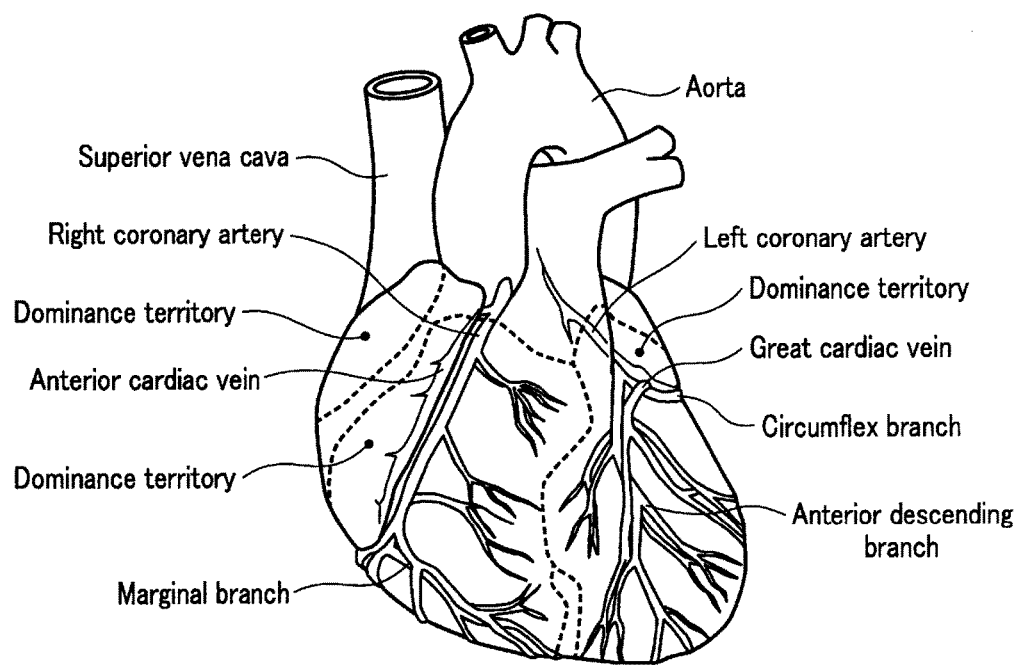
FIG. 2 is a schematic view illustrating an example of a territory map which is stored in a territory map storage unit according to the first embodiment.

FIG. 1 is a schematic view illustrating a configuration example of a medical image processing system including a medical image processing apparatus according to a first embodiment. FIG. 2 is a schematic view illustrating an example of a territory map which is stored in a territory map storage unit according to the embodiment. A medical image processing system 1 illustrated in FIG. 1 is a system in which a medical image processing apparatus 10, a CT (Computed Tomography) apparatus 20 and a PACS (Picture Archiving and Communication System) 30 are communicably connected via a network 40 such as a LAN (Local Area Network) or a public electronic communication network. Thus, the medical image processing apparatus 10 is provided with a communication interface 103 which enables communication with the CT apparatus 20 and PACS 50.

As illustrated in FIG. 1, the medical image processing apparatus 10 includes an image storage unit 101, a territory map storage unit 102, the communication interface 103, a controller 104, a heart region extraction unit 105, a cardiac muscle analysis unit 106, a coronary artery analysis unit 107, a responsible blood vessel specifying unit 108, an FFR calculator 109, a responsible stenosis specifying unit 110, a marker generator 111, and a display unit (a display) 112. Hereinafter, the functions of the respective components 101 to 112, which constitute the medical image processing apparatus 10, will be described in detail. It is noted that, the controller 104, the heart region extraction unit 105, the cardiac muscle analysis unit 106, the coronary artery analysis unit 107, the responsible blood vessel specifying unit 108, the FFR calculator 109, the responsible stenosis specifying unit 110 or the marker generator 111 is realized by at least one processing circuitry and at least one memory.

The image storage unit 101 is a storage device, such as memory, which stores time-series three-dimensional contrast-enhanced CT image data (hereinafter, simply referred to as "volume data") over a plurality of time phases relating to a chest region including the heart of the subject, as process images which are transmitted from the CT apparatus 20 or PACS 50 under the controller 104.

The territory map storage unit 102 is a storage device, such as memory, which stores a territory map (hereinafter referred to as "territory map") which defines, as illustrated in FIG. 2, a relationship between coronary arteries and dominance territories to which nutrition is supplied by the respective coronary arteries.

The heart region extraction unit 105 extracts a heart region from the volume data by a heart contour extraction process or the like.

The cardiac muscle analysis unit 106 extracts a cardiac muscle region from the heart region extracted by the heart region extraction unit 105, for example, by a threshold process by CT values corresponding to a contrast medium concentration. In addition, the cardiac muscle analysis unit 106 executes cardiac muscle perfusion analysis, that is, generates a time-concentration curve relating to a contrast medium with respect to each pixel or each local part within the extracted cardiac muscle region, and calculates, based on the time-concentration curve, the volume of a blood flow moving during a period from flow-in to flow-out of the contrast medium with respect to each pixel or each local part.

For example, in the photography using the CT apparatus, a non-ionic contrast medium is injected in the patient, and perfusion information of an internal organ can be depicted from the variation of the CT values. Thus, in the CT perfusion analysis, a time-based variation of a CT image (volume data), which is composed of, for example, 512×512 pixels, is measured from a variation of the CT value at each pixel, and the blood flow volume, etc. can be numerically expressed. In this manner, one color map representing the perfusion information (e.g. blood flow volume) of the internal organ is generated from the CT images of plural time phases.

Furthermore, the cardiac muscle analysis unit 106 specifies an ischemic region by a threshold process from a spatial distribution of the calculated blood flow volume.

The coronary artery analysis unit 107 extracts a plurality of coronary arteries from the heart region extracted by the heart region extraction unit 105, and further extracts at least one stenosed part from each extracted coronary artery. Specifically, the coronary artery analysis unit 107 executes analysis of an anatomical structure of a coronary artery and a plaque nature along a vessel center line of the coronary artery, the inner wall of the blood vessel, etc., and extracts volume data relating to the coronary artery, that is, extracts the coronary artery and a stenosed part located on the inner wall of this coronary artery. Incidentally, concrete examples of the plaque nature include a lipid amount, a serum cholesterol concentration, hardness, the degree of calcification, the thickness of a fibrous capsule (Thin-cap), and an FFR value (in this embodiment, it is assumed that the FFR value is calculated by the FFR calculator 109).

The responsible blood vessel specifying unit 108 refers to the territory map, which is stored in the territory map storage unit 102, for the ischemic region specified by the cardiac muscle analysis unit 106, thereby specifying a blood vessel (hereinafter referred to as "responsible blood vessel") which is inherently responsible for supply of nutrition to the ischemic region.

The FFR calculator 109 calculates, on a simulation basis, a value of FFR which corresponds to each stenosed part extracted by the coronary artery analysis unit 107. Specifically, the FFR calculator 109 first calculates, with respect to each stenosed part extracted by the coronary artery analysis unit 107, a tissue blood flow volume at least at one location on a downstream side of each stenosed part and a tissue blood flow volume at least at one location on an upstream side of each stenosed part, based on the color map generated by the cardiac muscle analysis unit 106. Then, the FFR calculator 109 calculates the FFR value at each location including at least the stenosed part by dividing the calculated tissue blood flow volume on the downstream side of the stenosed part by the calculated tissue blood flow volume on the upstream side of the stenosed part. In the meantime, in the present embodiment, although the FFR calculator 109 calculates the FFR value by the above-described calculation method, the calculation method of the FFR value is not limited to this. If the FFR value corresponding to each stenosed part can be calculated, any calculation method is applicable as the calculation method of the FFR value, which is used in the FFR calculator 109.

The responsible stenosis specifying unit 110 specifies a stenosed part (hereinafter referred to as "responsible stenosis") which is located on an inner wall of the responsible blood vessel specified by the responsible blood vessel specifying unit 108, among the stenosed parts extracted by the coronary artery analysis unit 107, that is, specifies a stenosed part having an FFR value of less than a threshold value, among responsible stenosis candidates, as the responsible stenosis.

The marker generator 111 generates data of markers which represent the responsible blood vessel specified by the responsible blood vessel specifying unit 108, the responsible stenosis specified by the responsible stenosis specifying unit 110, the FFR value calculated by the FFR calculator 109, and the responsible stenosis candidates extracted by the coronary artery analysis unit 107. These markers are displayed on the display unit 112 such that the markers are superimposed on a three-dimensional image generated by rendering, etc. from the volume data, or a two-dimensional image generated by cross-section conversion (Multi-Planar Reconstruction). Incidentally, the image, on which the markers generated by the marker generator 111 are superimposed, is not limited to the image derived from the volume data by the CT apparatus 20, but may be an image acquired from other modality such as an X-ray diagnosis apparatus.

Figure 3:
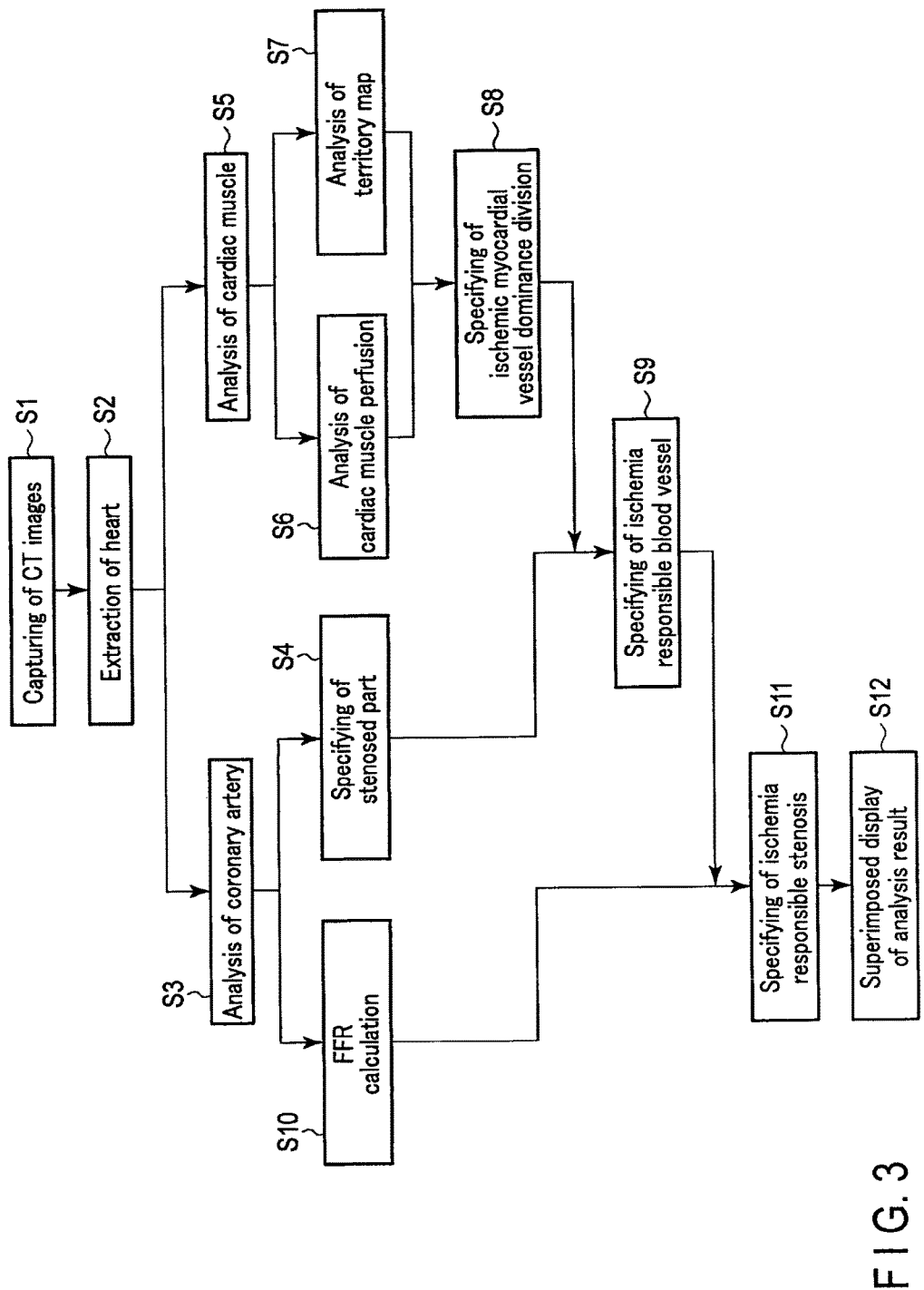
FIG. 3 is a flowchart illustrating an example of the operation of the medical image processing apparatus according to the first embodiment.

Referring now to schematic views of FIG. 2, and FIG. 4 to FIG. 7, and a flowchart illustrated in FIG. 3, a description is given of an example of the operation of the medical image processing apparatus 10 according to the present embodiment.

To start with, upon receiving an input of time-series volume data over a plurality of time phases relating to the chest region from the CT apparatus 20 or PACS 50 via the communication interface 103, the controller 104 writes the volume data, the input of which was accepted, in the image storage unit 101 (step S1).

Subsequently, the heart region extraction unit 105 reads out, under the controller 104, volume data of a specific time phase with a relatively small beat, as a process image, from the image storage unit 101, and extracts a heart region from the volume data (step S2).

Next, the coronary artery analysis unit 107 executes a coronary artery analysis process on a target that is the heart region extracted by the heart region extraction unit 105 (step S3, S4). Specifically, the coronary artery analysis unit 107 executes analysis of an anatomical structure of a coronary artery and a plaque nature along a vessel center line of the coronary artery, the inner wall of the blood vessel, etc., and extracts the coronary artery and a stenosed part located on the inner wall of this coronary artery. Thereafter, for example, as illustrated in FIG. 4(a) and FIG. 4(b), the coronary artery analysis unit 107 superimposes the anatomical structure of the coronary artery on the heart morphology image, and causes the display unit 112 to display the superimposed image as a three-dimensional image g1 or two-dimensional image g2. Incidentally, the operator can arbitrarily set the timing at which the image g1, g2 illustrated in FIG. 4(a), FIG. 4(b) is displayed on the display unit 112. Specifically, the image g1, g2 may be displayed in the course of the process, or may be displayed together with the result of the process.

Subsequently, the cardiac muscle analysis unit 106 extracts a cardiac muscle region from the heart region extracted by the heart region extraction unit 105, by a threshold process by CT values corresponding to a contrast medium concentration (step S5).

Figure 5:
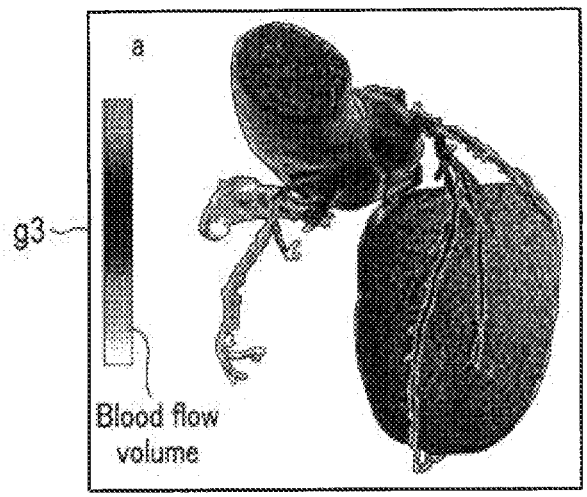
FIG. 5 is a schematic view illustrating an example of an analysis result by a cardiac muscle analysis unit according to the first embodiment.

Next, the cardiac muscle analysis unit 106 executes a CT perfusion analysis process on only the extracted cardiac muscle (step S6, S7, S8). Specifically, the cardiac muscle analysis unit 106 generates a time-concentration curve relating to a contrast medium with respect to each pixel or each local part within the extracted cardiac muscle region. Then, the cardiac muscle analysis unit 106 calculates, based on the time-concentration curve, the volume of a blood flow moving during a period from flow-in to flow-out of the contrast medium with respect to each pixel or each local part. Thereby, for example, as illustrated in FIG. 5, a color map g3, which indicates a spatial distribution of the blood flow volume, is generated. Then, the cardiac muscle analysis unit 106 specifies a region of less than a predetermined blood flow volume as an ischemic region, based on the generated color map g3, that is, the spatial distribution of the calculated blood flow volume.

Subsequently, the responsible blood vessel specifying unit 108 refers to the dominance map, which is stored in the territory map storage unit 102, as illustrated in FIG. 2, for the ischemic region specified by the cardiac muscle analysis unit 106, thereby specifying a responsible blood vessel (step S9).

Next, the FFR calculator 109 calculates, with respect to each stenosed part located on the inner wall of the responsible blood vessel specified by the responsible blood vessel specifying unit 108, a tissue blood flow volume on a downstream side of each stenosed part and a tissue blood flow volume on an upstream side of each stenosed part, based on the color map g3 generated by the cardiac muscle analysis unit 106. Then, the FFR calculator 109 calculates the FFR value at each location including at least the stenosed part by dividing the calculated tissue blood flow volume on the downstream side of the stenosed part by the calculated tissue blood flow volume on the upstream side of the stenosed part (step S10).

Subsequently, the responsible stenosis specifying unit 110 specifies, as a responsible stenosis, a stenosed part at which the FFR value calculated by the FFR calculator 109 is less than a threshold value (step S11).

Figure 6:
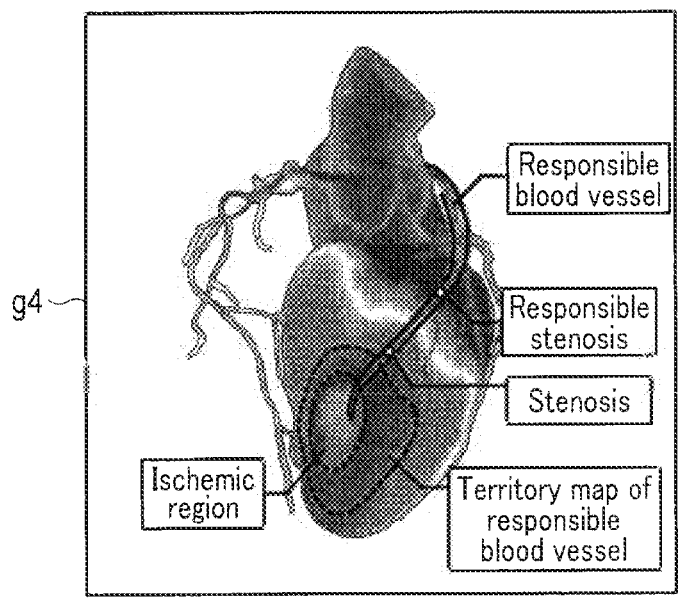
FIG. 6 is a schematic view illustrating an example of a three-dimensional image of a responsible blood vessel which is displayed by a display unit according the embodiment.
Figure 7:
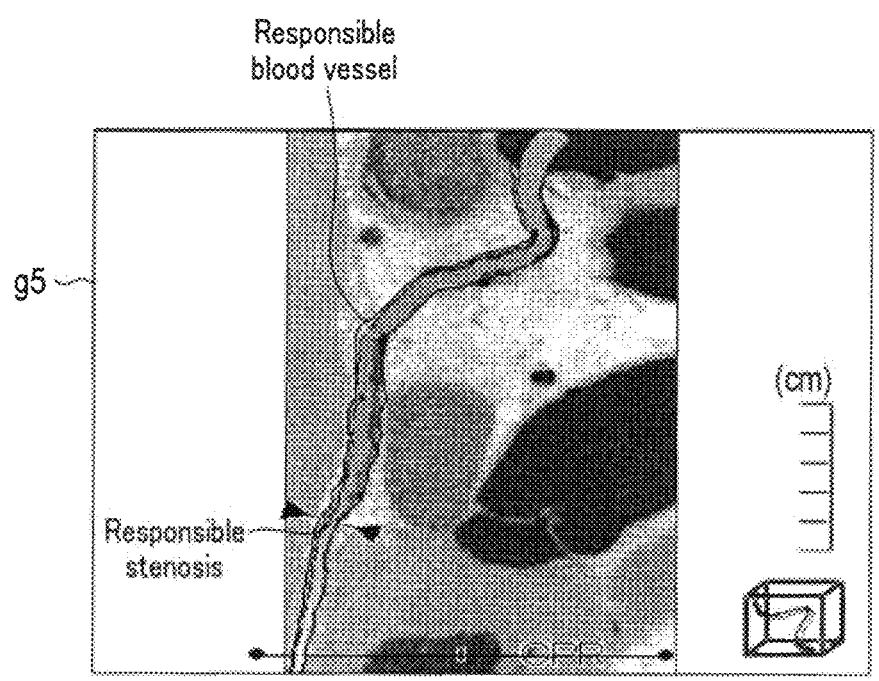
FIG. 7 is a schematic view illustrating an example of a two-dimensional image of a responsible blood vessel which is displayed by the display unit according the first embodiment.

Thereafter, for example, as illustrated in FIG. 6 and FIG. 7, the display unit 112 displays the markers generated by the marker generator 111, which represent the responsible blood vessel, the responsible stenosis and the FFR value, such that the markers are superimposed on a three-dimensional image g4 or a two-dimensional image g5, which is derived from the volume data (step S12).

The above-described embodiment is configured to include the heart region extraction unit 105, cardiac muscle analysis unit 106 and coronary artery analysis unit 107, which can extract the heart region, cardiac muscle region, coronary artery and stenosed part from the volume data by the CT apparatus 20; the responsible blood vessel specifying unit 108 which specifies the responsible blood vessel, based on the process result by the cardiac muscle analysis unit 106; the responsible stenosis specifying unit 110 which specifies the responsible stenosis, based on the process results by the coronary artery analysis unit 107, responsible blood vessel specifying unit 108 and FFR calculator 109; and the display unit 112 which displays the markers relating to the responsible blood vessel and responsible stenosis such that the markers are superimposed on the three-dimensional image or two-dimensional image, which is derived from the volume data. By this configuration, as illustrated in FIG. 6, the relationship in correspondency between the responsible stenosis and the dominance territory can be visually shown to the doctor, and thus the possibility of a human error can be reduced.

Additionally, in the present embodiment, since the FFR calculator 109 calculates FFR values on a simulation basis, that is, since nothing invasive, such as a pressure wire, is used, the load on the patient at a time of examination can be reduced.

In the meantime, in the present embodiment, although images, which the display unit 112 displays, are illustrated in FIG. 6 and FIG. 7 by way of example, the images displayed on the display unit 112 are not limited to these. For example, images g6 and g7 as illustrated in FIG. 8A and FIG. 8B may be displayed. FIG. 8A and FIG. 8B illustrate examples of the images g6 and g7 in which the degrees of priority of treatment of stenosed parts are ranked based on the FFR values calculated by the FFR calculator 109, and this process result is superimposed as markers. Here, a marker (circle mark), which indicates a stenosed part with a higher degree of priority of treatment, is larger. In addition, FIG. 8A illustrates an example of the image g6, in which a bar graph indicative of the analysis result of the plaque nature by the coronary artery analysis unit 107 is superimposed as a marker, in addition to the degree of priority. Incidentally, in the image g6 illustrated in FIG. 8A, the properties of blood, etc., in addition to the analysis result of the plaque nature, may be superimposed as markers. Besides, when a plurality of responsible blood vessels exist, it is possible to display an image on the display unit 112, such that the degrees of priority of treatment of stenosed parts over the plural responsible blood vessels are ranked, and then the process result is superimposed as markers.

Additionally, according to the medical image processing apparatus 10 relating to the embodiment, when the dominance map is referred to by the responsible blood vessel specifying unit 108, it is possible to detect whether a territory of another artery extends into a part of a territory to which blood should be supplied by a certain artery, and to suggest a possibility of blood supply by a collateral vessel if such extension of the territory of the another artery is detected. In general, if a collateral vessel is present, the reliability of the FFR value lowers. Thus, for example, as illustrated in FIG. 9, by displaying on the display unit 112 an image g8 which suggests the presence of the collateral vessel, the possibility of a human error can further be reduced.

Furthermore, according to the medical image processing apparatus 10 relating to the embodiment, after the responsible stenosis is specified by the responsible stenosis specifying unit 110, the diameter in cross section and the length of the responsible stenosis can be measured from the two-dimensional image derived from the volume data, and the optimal size of the catheter/stent can be suggested based on the measurement result. Specifically, for example, as illustrated in FIG. 10, by displaying on the display unit 112 an image g9 which suggests the optimal size of the catheter/stent, the possibility of a human error can further be reduced.

Additionally, according to the medical image processing apparatus 10 relating to the embodiment, when the presence of ischemic regions at plural locations has been indicated by the cardiac muscle analysis unit 106, the thickness of the cardiac muscle, etc. can be measured from the volume data, and, based on the result of this measurement, such setting can be added that a blood vessel corresponding to a dominance territory of a necrosed cardiac muscle is not specified as a responsible blood vessel.

Furthermore, according to the medical image processing apparatus 10 relating to the embodiment, when a desired three-dimensional image was displayed by the display unit 112, if an input indicating selection of a responsible blood vessel or a responsible stenosis is accepted from an input interface (not shown) such as a mouse, a keyboard or a touch panel, it is also possible to automatically rotate the three-dimensional image at such an angle that the selected responsible blood vessel or responsible stenosis can easily be observed.

Second Embodiment

Figure 11:
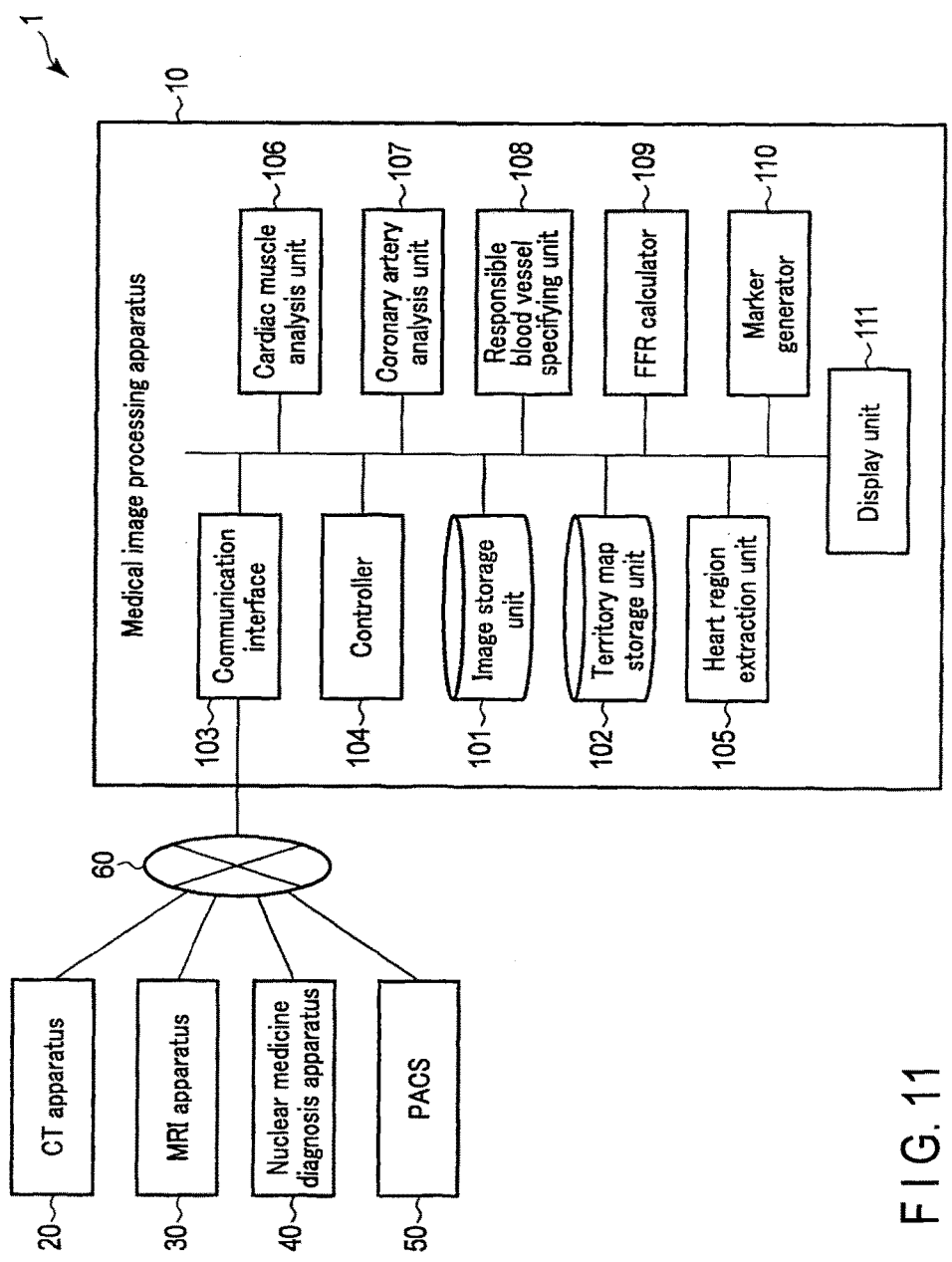
FIG. 11 is a schematic view illustrating a configuration example of a medical imaging system including a medical image processing apparatus according to a second embodiment.

FIG. 11 is a schematic view illustrating a configuration example of a medical image processing system including a medical image processing apparatus according to a second embodiment. A medical image processing system 1 illustrated in FIG. 11 is a system in which a medical image processing apparatus 10, a CT (Computed Tomography) apparatus 20, an MRI (Magnetic Resonance Imaging) apparatus 30, a nuclear medicine diagnosis apparatus 40, and a PACS (Picture Archiving and Communication System) 50 are communicably connected via a network 60 such as a LAN (Local Area Network) or a public electronic communication network. Thus, the medical image processing apparatus 10 is provided with a communication interface 103 which enables communication with the CT apparatus 20, MRI apparatus 30, nuclear medicine diagnosis apparatus 40 and PACS 50.

As illustrated in FIG. 11, the medical image processing apparatus 10 includes an image storage unit 101, a territory map storage unit 102, the communication interface 103, a controller 104, a heart region extraction unit 105, a cardiac muscle analysis unit 106, a coronary artery analysis unit 107, a responsible blood vessel specifying unit 108, an FFR calculator 109, a marker generator 111, and a display unit 111. Hereinafter, a description is given of only the structure which is different from the medical image processing apparatus 1 illustrated in the first embodiment.

The image storage unit 101 is a storage device which stores time-series three-dimensional contrast-enhanced CT image data over a plurality of time phases relating to a chest region including the heart of the subject, as process images which are transmitted from the CT apparatus 20 or PACS 50 under the controller 104.

The territory map storage unit 102 is a storage device which stores a territory map which defines, as illustrated in FIG. 2, a relationship between coronary arteries and dominance territories to which nutrition is supplied by the respective coronary arteries.

The heart region extraction unit 105 extracts a heart region from the volume data by a heart contour extraction process or the like.

The cardiac muscle analysis unit 106 extracts a cardiac muscle region from the heart region extracted by the heart region extraction unit 105, for example, by a threshold process by CT values corresponding to a contrast medium concentration. In addition, the cardiac muscle analysis unit 106 specifies a necrosed cardiac muscle region of the extracted cardiac muscle region, that is, a myocardial infarction region which contributes to myocardial infarction, by late gadolinium enhancement by the MRI apparatus 30, saccharometabolism measurement by the nuclear medicine diagnosis apparatus 40, etc.

Furthermore, the cardiac muscle analysis unit 106 executes cardiac muscle perfusion analysis, that is, calculates the volume of a blood flow moving during a period from flow-in to flow-out of a contrast medium with respect to each pixel or each local part within the extracted cardiac muscle region. For example, in the photography using the CT apparatus 20, a non-ionic contrast medium is injected in the patient, and perfusion information of an internal organ can be depicted from the variation of the CT value. Thus, in the CT perfusion analysis, a time-based variation of a CT image (volume data), which is composed of, for example, 512×512 pixels, is measured from a variation of the CT value at each pixel, and the blood flow volume, etc. can be numerically expressed. In this manner, one color map representing the perfusion information (e.g. blood flow volume) of the internal organ is generated from the CT images of plural time phases.

Specifically, the cardiac muscle analysis unit 106 can specify not only the myocardial infarction region, but can also specify, for example, a part with a decreased blood flow, that is, an ischemic region, by a threshold process from a spatial distribution of the calculated blood flow volume.

The coronary artery analysis unit 107 extracts a plurality of coronary arteries from the heart region extracted by the heart region extraction unit 105, and further extracts at least one stenosed part from each extracted coronary artery. Specifically, the coronary artery analysis unit 107 executes analysis of an anatomical structure of a coronary artery and a plaque nature along a vessel center line of the coronary artery, the inner wall of the blood vessel, etc., and extracts volume data relating to the coronary artery, that is, extracts the coronary artery and a stenosed part located on the inner wall of this coronary artery. Incidentally, concrete examples of the plaque nature include a lipid amount, a serum cholesterol concentration, hardness, the degree of calcification, and the thickness of a fibrous capsule (Thin-cap).

The responsible blood vessel specifying unit 108 refers to the dominance map, which is stored in the territory map storage unit 102, for the myocardial infarction region specified by the cardiac muscle analysis unit 106, thereby specifying a blood vessel (hereinafter referred to as "infarction responsible blood vessel") which is inherently responsible for supply of nutrition to the myocardial infarction region.

In the meantime, when the ischemic region, in place of the myocardial infarction region, is specified by the cardiac muscle analysis unit 106, the responsible blood vessel specifying unit 108 refers to the dominance map, which is stored in the territory map storage unit 102, for the ischemic region specified by the cardiac muscle analysis unit 106, thereby specifying a blood vessel (hereinafter referred to as "ischemia responsible blood vessel") which is inherently responsible for supply of nutrition to the ischemic region.

The FFR calculator 109 calculates, on a simulation basis, FFR values relating a plurality of locations including at least a stenosed part of each coronary artery extracted by the coronary artery analysis unit 107. Specifically, the FFR calculator 109 first calculates a tissue blood flow volume at least at one location on a downstream side of the stenosed part in the coronary artery and a tissue blood flow volume at least at one location on an upstream side of the stenosed part in the coronary artery, based on the color map generated by the cardiac muscle analysis unit 106. Then, the FFR calculator 109 calculates the FFR value at each location including at least the stenosed part by dividing the calculated tissue blood flow volume on the downstream side of the stenosed part by the calculated tissue blood flow volume on the upstream side of the stenosed part. In the meantime, the description has been given here of the case of calculating the FFR value corresponding to one stenosed part in the coronary artery. However, for example, in the case of calculating the FFR value of the entirety of the coronary artery, the tissue blood flow volume on the upstream side of the stenosed part, which is located on the most upstream side in the coronary artery may be fixed as a reference value, and tissue blood flow volumes at other plural locations may be set as variables (it is assumed that the FFR calculator 109 has calculated the tissue blood flow volumes at plural locations in the coronary artery). Thereby, the FFR calculator 109 can calculate the FFR values corresponding to the plural locations, that is, the FFR values of the entirety of the coronary artery.

The marker generator 111 generates data of markers (marks) which represent the infarction responsible blood vessel (or ischemia responsible blood vessel) specified by the responsible blood vessel specifying unit 108, and the FFR values calculated by the FFR calculator 109. These markers are displayed on the display unit 111 such that the markers are superimposed on a three-dimensional image generated by rendering, etc. from the volume data, or a two-dimensional image generated by cross-section conversion (Multi-Planar Reconstruction). Incidentally, the image, on which the markers generated by the marker generator 111 are superimposed, is not limited to the image derived from the volume data by the CT apparatus 20, but may be an image acquired from other modality such as an X-ray diagnosis apparatus.

Figure 12:
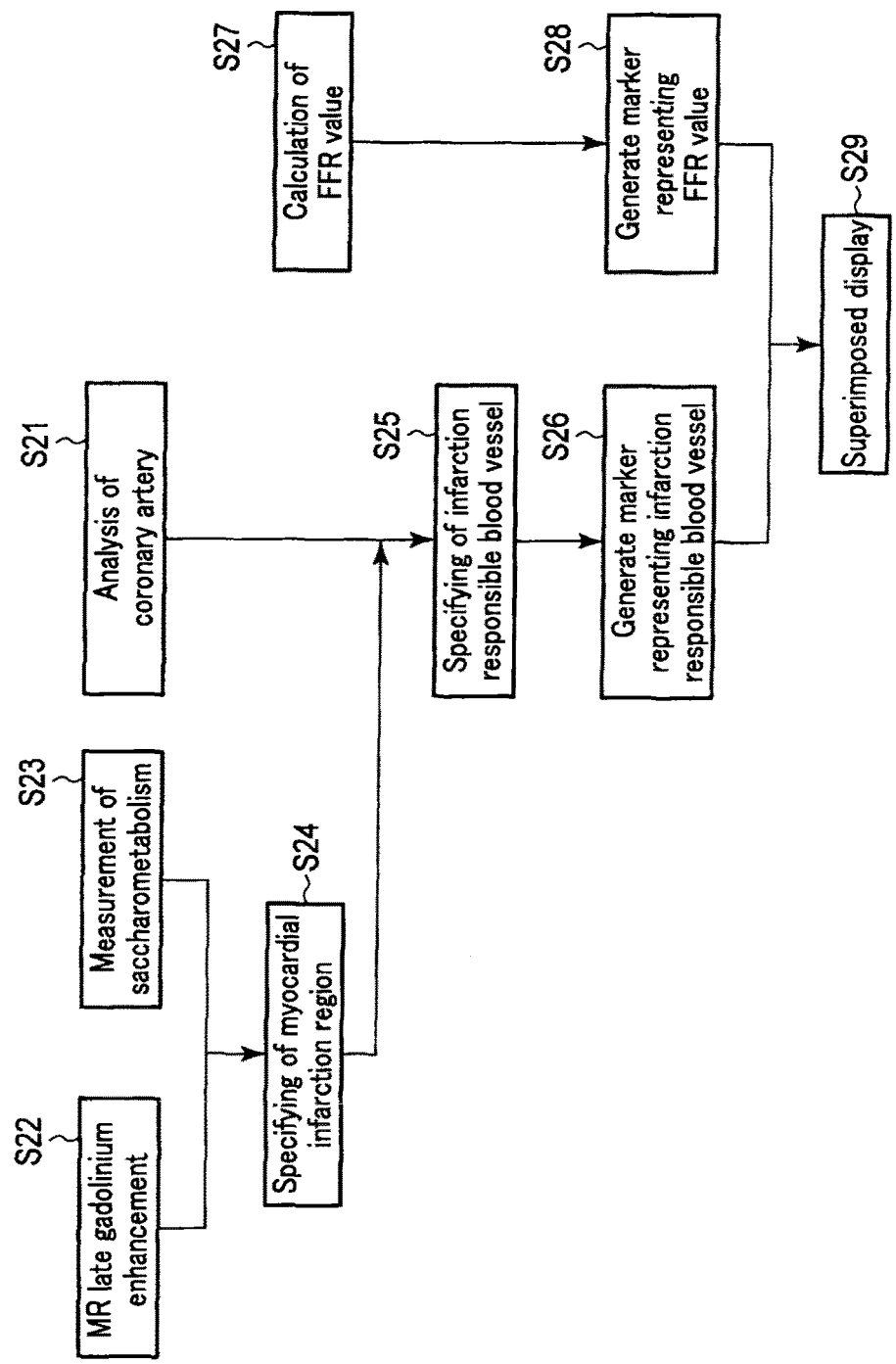
FIG. 12 is a flowchart illustrating an example of the operation of the medical image processing apparatus according to the second embodiment.

Referring now to schematic views of FIG. 2, and FIG. 13 to FIG. 16, and a flowchart of FIG. 12, a description is given of an example of the operation of the medical image processing apparatus 10 according to the present embodiment.

Here, it is assumed, however, that the time-series volume data over a plurality of time phases relating to the chest region from the CT apparatus 20 or PACS 50 is prestored in the image storage unit 101. In addition, it is assumed that the heart region extraction unit 105 has already read out, under the controller 104, volume data of a specific time phase with a relatively small beat, as a process image, from the image storage unit 101, and has already extracted a heart region from the volume data.

To start with, the coronary artery analysis unit 107 executes a coronary artery analysis process on a target that is the heart region extracted by the heart region extraction unit 105 (step S21). Specifically, the coronary artery analysis unit 107 executes analysis of an anatomical structure of a coronary artery and a plaque nature along a vessel center line of the coronary artery, the inner wall of the blood vessel, etc., and extracts the coronary artery and a stenosed part located on the inner wall of this coronary artery.

Subsequently, the cardiac muscle analysis unit 106 extracts a cardiac muscle region from the heart region extracted by the heart region extraction unit 105, by a threshold process by CT values corresponding to a contrast medium concentration. Thereafter, the cardiac muscle analysis unit 106 specifies a necrosed cardiac muscle region of the extracted cardiac muscle region, that is, a myocardial infarction region which contributes to myocardial infarction, by late gadolinium enhancement by the MRI apparatus 30, saccharometabolism measurement by the nuclear medicine diagnosis apparatus 40, etc. (step S22, S23, S24).

Next, the responsible blood vessel specifying unit 108 refers to the dominance map, which is stored in the territory map storage unit 102, for the myocardial infarction region specified by the cardiac muscle analysis unit 106, thereby specifying an infarction responsible blood vessel from each coronary artery extracted by the coronary artery analysis unit 107 (step S25).

Figure 13:
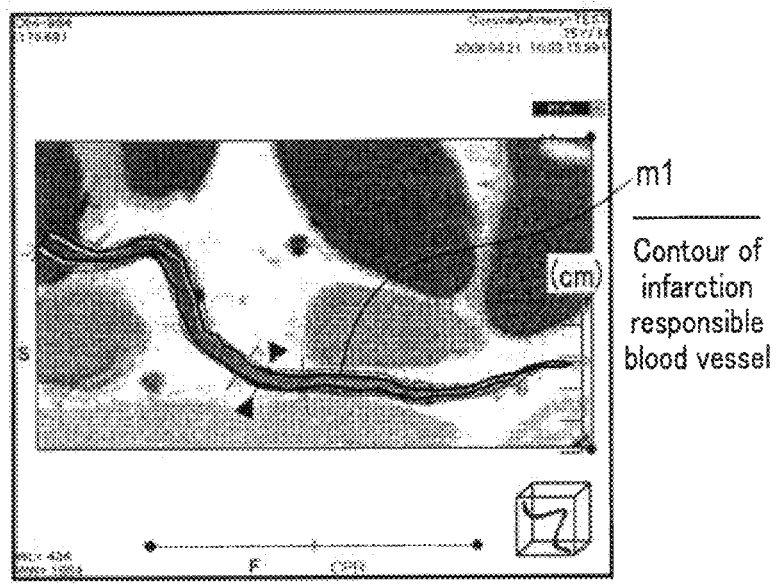
FIG. 13 is a schematic view illustrating an example of a marker representing a contour of an infarction responsible blood vessel, which is generated by a marker generator according to the second embodiment.

Subsequently, the marker generator 111 generates data of a marker which represents the infarction responsible blood vessel specified by the responsible blood vessel specifying unit 108 (step S26). Specifically, for example, as illustrated in FIG. 13, the marker generator 111 generates a marker m1 representing a contour of the infarction responsible blood vessel.

Next, the FFR calculator 109 calculates the FFR values corresponding to the entirety of the coronary artery with respect to each coronary artery extracted by the coronary artery analysis unit 107 (step S27).

Figure 14:
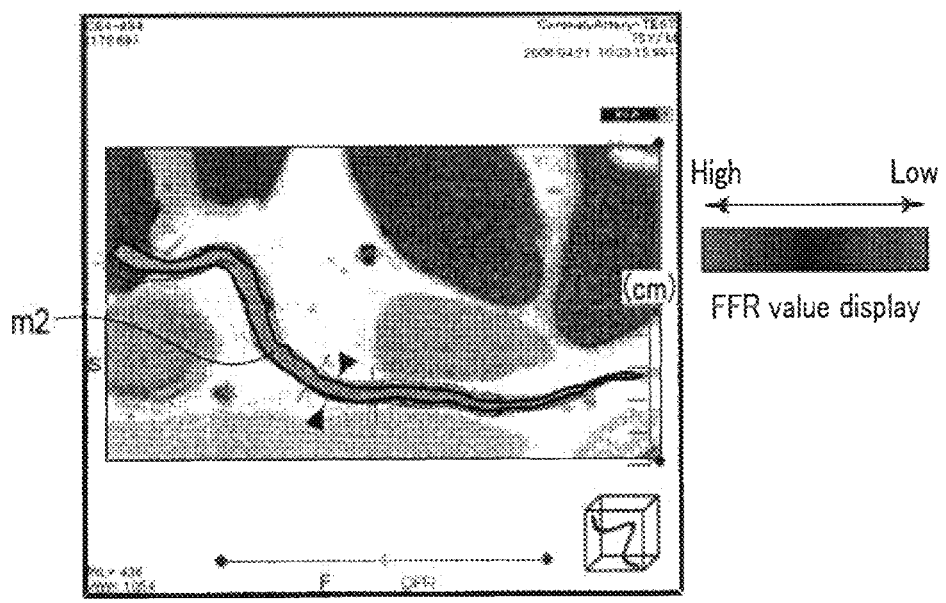
FIG. 14 is a schematic view illustrating an example of a marker representing a transition of FFR values, which is generated by the marker generator according to the second embodiment.

Subsequently, the marker generator 111 generates a marker which represents the FFR value corresponding to each coronary artery, which was calculated by the FFR calculator 109 (step S28). Specifically, for example, as illustrated in FIG. 14, the marker generator 111 generates a marker m2 which represents a transition of the FFR value of each coronary artery.

Thereafter, for example, as illustrated in FIG. 15, the display unit 111 displays the marker m1 representing the infarction responsible blood vessel and the marker m2 representing the transition of the FFR value of each coronary artery, which were generated by the marker generator 111, such that the marker m1 and marker m2 are superimposed on a two-dimensional image g1 which was derived from the volume data (step S29). Incidentally, the image, which the display unit 111 displays, is not limited to the two-dimensional image g1, but may be an image on which the markers are superimposed on a three-dimensional image g2 which was derived from the volume data, for example, as illustrated in FIG. 16, or an image acquired from other modality.

Figure 17:
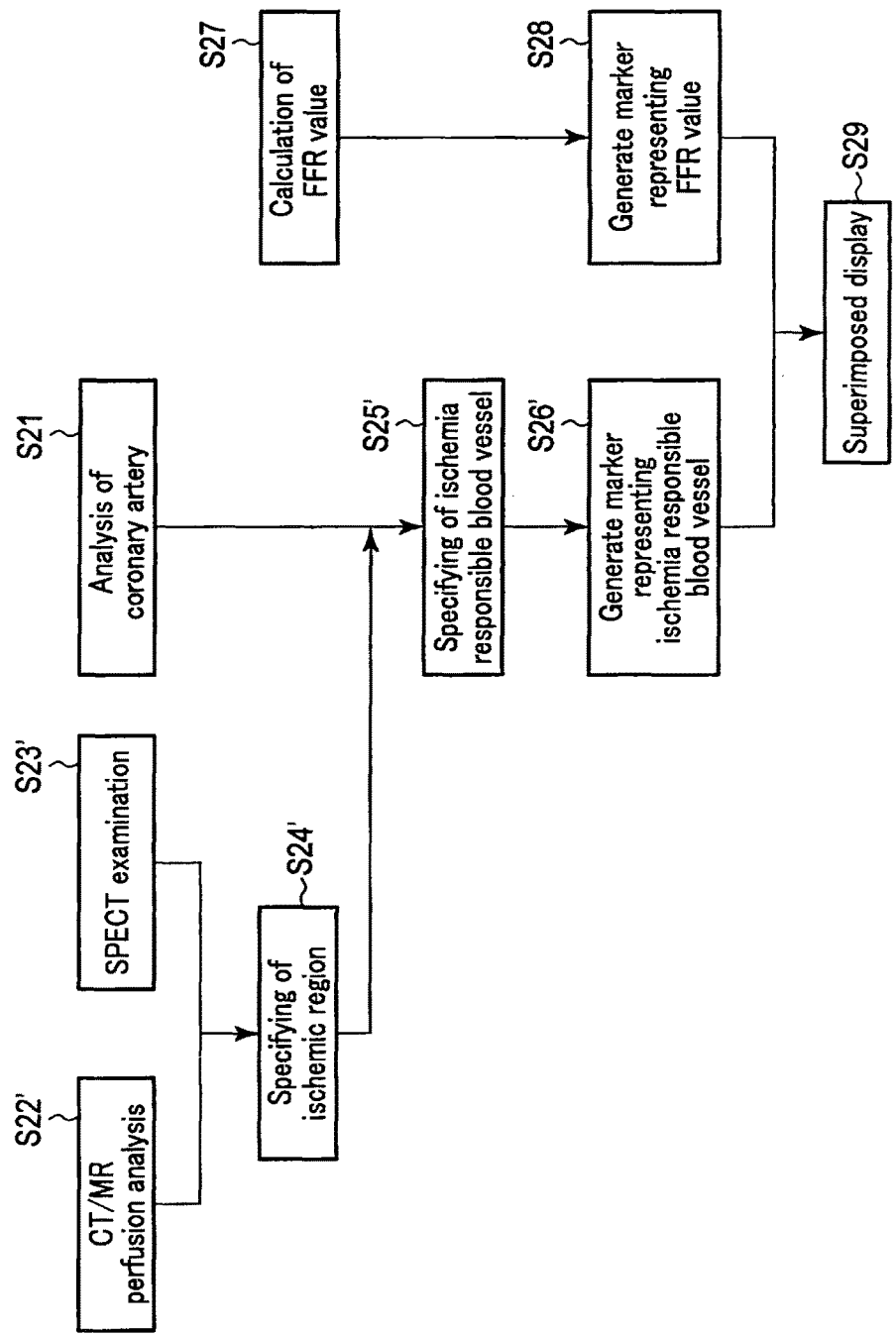
FIG. 17 is a flowchart illustrating another example of the operation of the medical image processing apparatus according to the second embodiment.

In the meantime, in the above description of the example of the operation, the case was described in which the responsible blood vessel specifying unit 108 specifies the infarction responsible blood vessel. However, for example, as illustrated in a flowchart of FIG. 17, also in the case in which the responsible blood vessel specifying unit 108 specifies the ischemia responsible blood vessel, the operation is the same as in the above example, except that the medical image processing apparatus 10 specifies the ischemic region by a cardiac muscle perfusion analysis by the CT apparatus 20 or MRI apparatus 30, a SPECT examination by the nuclear medicine diagnosis apparatus 40, etc. (step S22', S23', S24'), specifies the ischemia responsible blood vessel from the specified ischemic region (step S25'), and generates a marker representing the specified ischemia responsible blood vessel (step 26').

The above-described second embodiment is configured to include the heart region extraction unit 105, cardiac muscle analysis unit 106 and coronary artery analysis unit 107, which can extract the heart region, cardiac muscle region, coronary artery, stenosed part and myocardial infarction region from the volume data by the CT apparatus 20; the responsible blood vessel specifying unit 108 which specifies the infarction responsible blood vessel, based on the process result by the cardiac muscle analysis unit 106; and the display unit 111 which displays the markers representing the infarction responsible blood vessel and the FFR value calculated by the FFR calculator 109, such that the markers are superimposed on the two-dimensional image or three-dimensional image, which is derived from the volume data. By this configuration, it is possible to show the doctor that the reliability of the FFR value of the part, on which the marker representing the infarction responsible blood vessel is displayed by superimposition, is low.

Additionally, in the present embodiment, since the FFR calculator 109 calculates FFR values on a simulation basis, that is, since nothing invasive, such as a pressure wire, is used, the load on the patient at a time of examination can be reduced.

Third Embodiment

Figure 18:
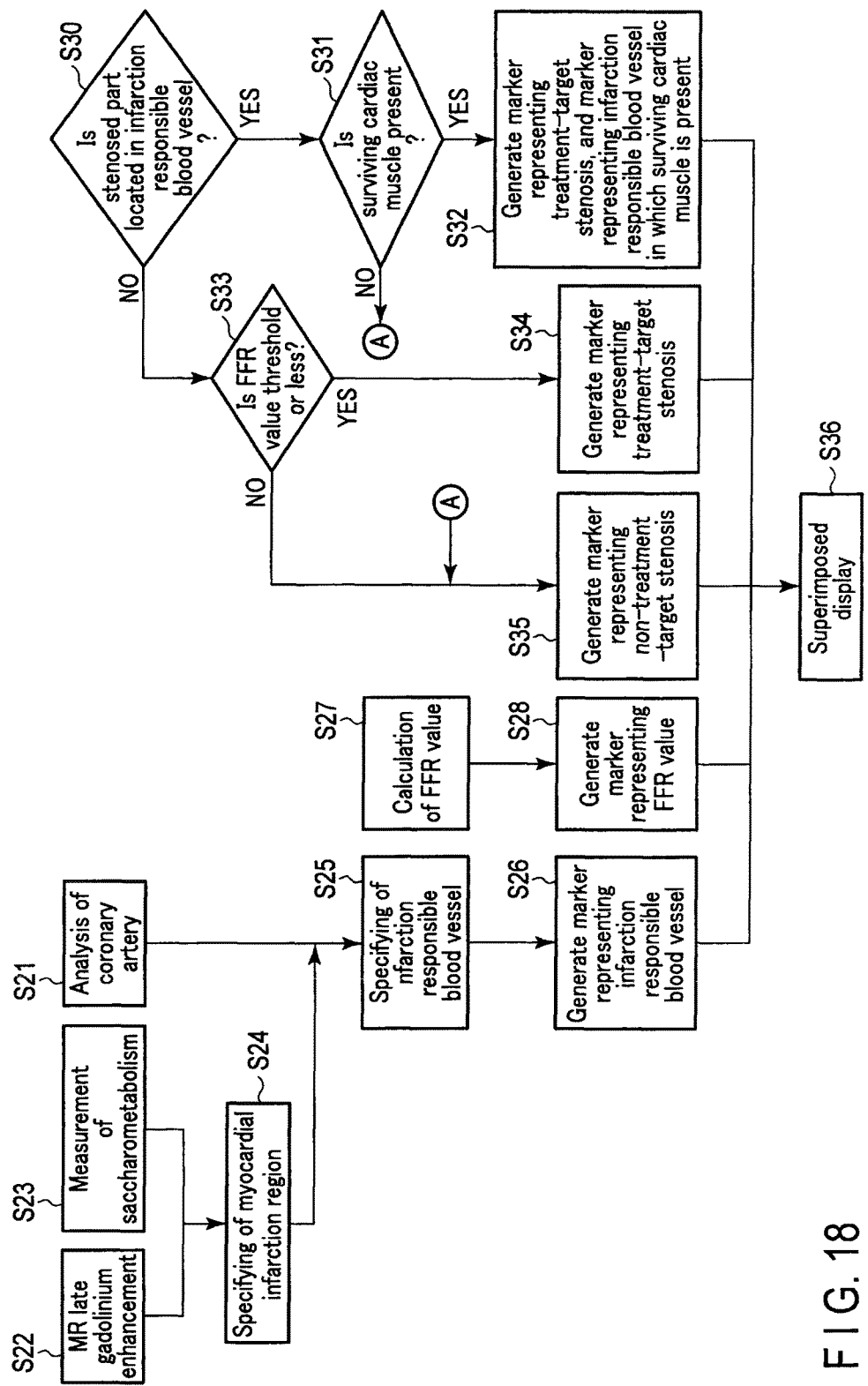
FIG. 18 is a flowchart illustrating an example of the operation of a medical image processing apparatus according to a third embodiment.
Figure 20:
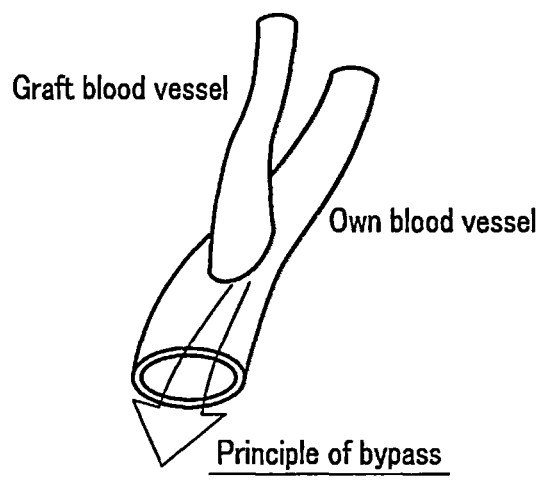
FIG. 20 is a schematic view for explaining the principle of bypass surgery.
Figure 21:
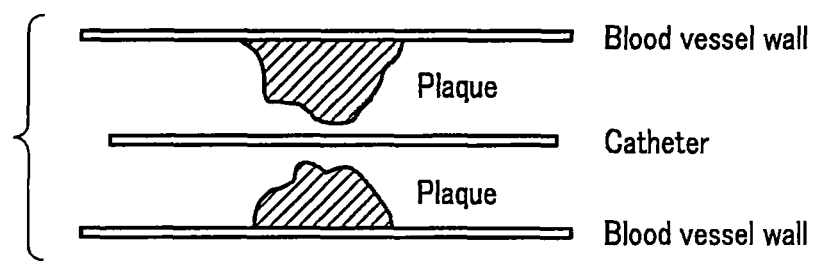
FIG. 21 is a schematic view for explaining the principle of a catheter operation on a blood vessel stenosis.
Figure 22:
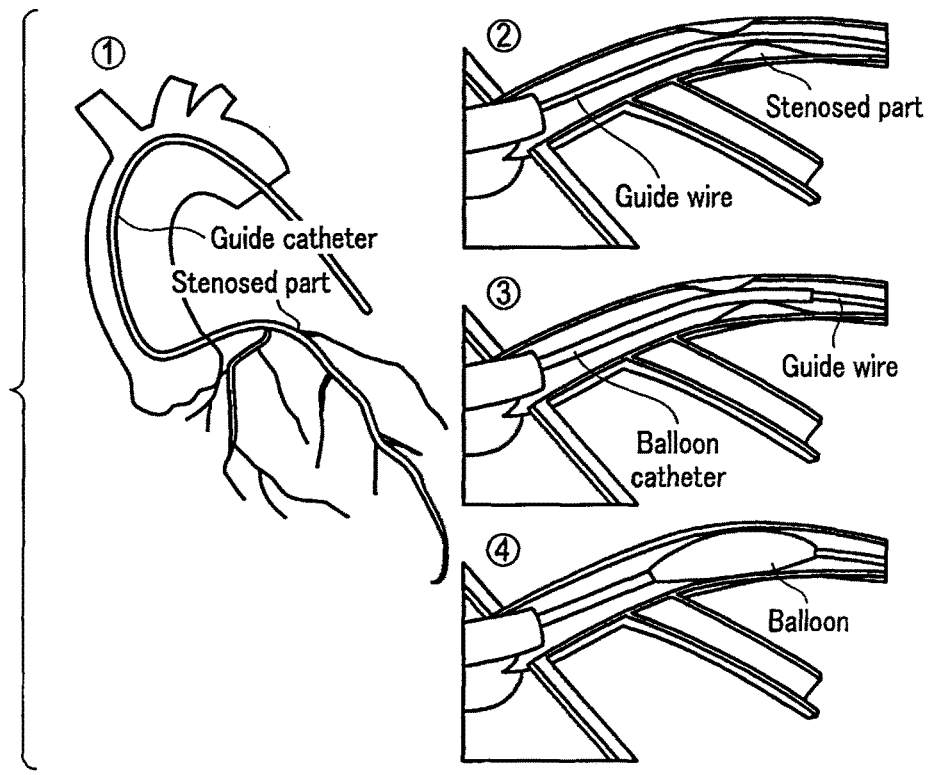
FIG. 22 is a schematic view for explaining the principle of a balloon catheter operation.
Figure 23:
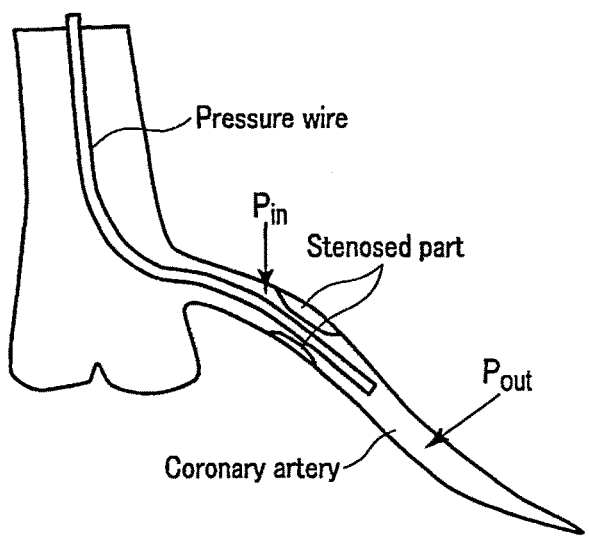
FIG. 23 is a schematic view for explaining an insertion method of a pressure wire into a coronary artery.

Next, a medical image processing apparatus according to a third embodiment is described with referenced to the above-described FIG. 11. In the present embodiment, a function of determining whether a stenosed part in a coronary artery is a treatment-target stenosis or a non-treatment-target stenosis is added to the medical image processing apparatus 10 illustrated in the second embodiment. Incidentally, only functions different from the second embodiment will be described with reference to a flowchart of FIG. 18 and a schematic view of FIG. 19. Specifically, since the process of steps S21 to S28 is the same as in the above-described second embodiment, a detailed description thereof is omitted here, and the process of steps S30 to S36 will mainly be described below.

The coronary artery analysis unit 107 determines, with respect to each stenosed part extracted in the process of step S21, whether the stenosed part is a stenosis located in the infarction responsible blood vessel (step S30).

If the result of determination by the process of step S30 indicates that the stenosed part is a stenosis located in the infarction responsible blood vessel (Yes in step S30), the cardiac muscle analysis unit 106 determines whether a surviving cardiac muscle is present in the myocardial infarction region specified in the process of step S24 (step S31). Specifically, the cardiac muscle analysis unit 106 determines whether the myocardial infarction region reaches half the thickness of the cardiac muscle, from the late gadolinium enhancement by the MRI apparatus 30, etc. If the result of the determination indicates that the myocardial infarction region reaches half the thickness of the cardiac muscle, it is deemed that a surviving cardiac muscle is absent. If the result of the determination indicates "NO", it is deemed that a surviving cardiac muscle is present. Incidentally, if the result of the determination by the process of step S31 indicates "NO" (No in step S31), the process goes to step S35 which is to be described later.

If the result of the determination by the process of step S31 indicates that a surviving cardiac muscle is present (Yes in step S31), the marker generator 111 generates a marker representing the infarction responsible blood vessel in which the surviving cardia muscle is present, and a marker representing a treatment-target stenosis (step S32). Specifically, for example, as illustrated in FIG. 19, the marker generator 111 generates a marker m3 representing the contour of the infarction responsible blood vessel in which the surviving cardia muscle is present, and a marker m4 representing the treatment-target stenosis.

Here, if the result of the determination by the process of step S30 indicates "NO" (No in step S30), the coronary artery analysis unit 107 determines whether the FFR value corresponding to the stenosed part, among the FFR values of the respective coronary arteries calculated in the process of step S27, is a threshold value or less (step S33).

If the result of the determination by the process of step S33 indicates that the FFR value corresponding to the stenosed part is the threshold value or less (Yes in step S33), the marker generator 111 generates a marker representing a treatment-target stenosis (step S34). Specifically, the marker generator 111 generates a marker corresponding to the marker m4 illustrated in FIG. 19.

If the result of the determination by the process of step S33 indicates "NO" (No in step S33), the marker generator 111 generates a marker representing a non-treatment-target stenosis (step S35). Specifically, for example, as illustrated in FIG. 19, the marker generator 111 generates a marker m5 representing a non-treatment-target stenosis.

Thereafter, the display unit 111 displays the marker m1 representing the infarction responsible blood vessel, the marker m2 representing the transition of the FFR value of each coronary artery, the marker m3 representing the infarction responsible blood vessel in which the surviving cardia muscle is present, and the marker m4 representing the treatment-target stenosis, which were generated by the marker generator 111, such that these markers are superimposed on the three-dimensional image g3 which was derived from the volume data (step S36). Incidentally, the image, which the display unit 111 displays, is not limited to the three-dimensional image g3, but may be an image on which the markers are superimposed on a two-dimensional image derived from the volume data, or an image acquired from other modality. In addition, when the marker m1 representing the infarction responsible blood vessel, and the marker m3 representing the infarction responsible blood vessel in which the surviving cardia muscle is present, are superimposed at the same position on the image, it is assumed the marker m3 is preferentially displayed.

The above-described third embodiment is configured to include the cardiac muscle analysis unit 106 and coronary artery analysis unit 107, which determine whether a surviving cardiac muscle is present in the myocardial infarction region, and whether the stenosed part in the coronary artery is a treatment-target stenosis or a non-treatment-target stenosis; and the display unit 111 which displays the marker representing the infarction responsible blood vessel in which the surviving cardia muscle is present, the marker representing the treatment-target stenosis and the marker representing the non-treatment-target stenosis, such that these markers are superimposed on the three-dimensional image or two-dimensional image which was derived from the volume data. By this configuration, compared to the first embodiment, a greater amount of information can be presented to the doctor.

According to at least one of the above-described second and third embodiments, it is possible to show the doctor that the reliability of the FFR value is low, whether a surviving cardiac muscle is present or not, and whether a stenosed part is a stenosis which is suitable for treatment or not. Therefore, the possibility of a human error can be reduced.

The above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in storage memory 12. In this case, the processing circuitry reads programs incorporated in circuitry and executes the programs to realize predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

What is claimed is:

1. A medical image processing apparatus comprising:
a first extraction unit implemented by processing circuitry configured to extract a plurality of coronary arteries depicted in data of images of a plurality of time phases relating to the heart, and to extract at least one stenosed part depicted in each of the extracted coronary arteries;
a calculation unit implemented by processing circuitry configured to calculate a pressure gradient of each of the extracted coronary arteries, based on tissue blood flow volumes of the plurality of extracted coronary arteries;
a second extraction unit implemented by processing circuitry configured to extract an ischemic region depicted in the images;
a specifying unit implemented by processing circuitry configured to specify a responsible blood vessel of the ischemic region by referring to a dominance map, in which each of the extracted coronary arteries and a dominance territory are associated, for the extracted ischemic region, and to specify a responsible stenosis, based on the pressure gradient corresponding to a stenosed part in the specified responsible blood vessel; and
a display configured to display an image in which the specified responsible stenosis and the specified responsible blood vessel are depicted, together with information indicative of the responsible stenosis and the responsible blood vessel,
wherein the extracted coronary arteries supply nutrition to the dominance territory, and the responsible blood vessel is inherently responsible for supply of the nutrition to the ischemic region, and
wherein the dominance map is predetermined, and associates the dominance territory of a cardiac muscle with the extracted coronary arteries being inherently responsible for supply of the nutrition to the dominance territory.

2. The medical image processing apparatus of claim 1, wherein the display is configured to display the image in which the specified responsible stenosis is depicted, together with a pressure gradient corresponding to the responsible stenosis.

3. The medical image processing apparatus of claim 1, wherein the specifying unit is configured to refer to the dominance map for the extracted ischemic region, thereby specifying whether a collateral vessel is present in the ischemic region, and
the display is configured to effect display of information indicating whether a collateral vessel is present in the ischemic region.

4. The medical image processing apparatus of claim 1, wherein the extraction unit is configured to generate a tissue blood flow image relating to a cardiac muscle from the images, and to extract the ischemic region from the tissue blood flow image.

5. The medical image processing apparatus of claim 1, further comprising a priority order determination unit implemented by processing circuitry configured to rank a degree of priority of treatment of a stenosed part, based on the pressure gradient corresponding to the stenosed part in the specified responsible blood vessel, and
the display is configured to display information indicative of the degree of priority of treatment which is determined.

6. The medical image processing apparatus of claim 1, wherein the second extraction unit is configured to extract a myocardial infarction region from the ischemic region,
the specifying unit is configured to refer to the dominance map for the extracted myocardial infarction region, thereby specifying a responsible blood vessel of the myocardial infarction region from each of the coronary arteries, and
the display displays an image in which the specified responsible blood vessel is depicted, together with information indicative of the responsible blood vessel.

7. The medical image processing apparatus of claim 1, wherein the specifying unit is configured to specify at least one of a catheter and a stent for use in treatment of the responsible stenosis, based on a size of the specified responsible stenosis, and
the display is configured to display the at least specified one of the catheter and the stent.

8. The medical image processing apparatus of claim 1, wherein the display displays the image such that the image is rotated in accordance with a position of the specified responsible stenosis.

9. A medical image processing method comprising:
extracting a plurality of coronary arteries depicted in data of images of a plurality of time phases relating to the heart, and extracting at least one stenosed part depicted in each of the extracted coronary arteries;
calculating a pressure gradient of each of the extracted coronary arteries, based on tissue blood flow volumes of the plurality of extracted coronary arteries;
extracting an ischemic region depicted in the images;
specifying a responsible blood vessel of the ischemic region by referring to a dominance map, in which each of the extracted coronary arteries and a dominance territory are associated, for the extracted ischemic region, and specifying a responsible stenosis, based on the pressure gradient corresponding to a stenosed part in the specified responsible blood vessel; and
displaying an image in which the specified responsible stenosis and the specified responsible blood vessel are depicted, together with information indicative of the responsible stenosis and the responsible blood vessel,
wherein the extracted coronary arteries supply nutrition to the dominance territory, and the responsible blood vessel is inherently responsible for supply of the nutrition to the ischemic region, and
wherein the dominance map is predetermined, and associates the dominance territory of a cardiac muscle with the extracted coronary arteries being inherently responsible for supply of the nutrition to the dominance territory.

10. The medical image processing apparatus of claim 1, wherein the display is configured to display the image in which the ischemic region, the dominance territory associated with the responsible blood vessel, and the stenosed part in the specified responsible blood vessel, together with information indicative of the ischemic region, the dominance territory associated with the responsible blood vessel, and the stenosed part in the specified responsible blood vessel.

* * * * *